(12) United States Patent
Can et al.

(10) Patent No.: US 8,369,600 B2
(45) Date of Patent: Feb. 5, 2013

(54) METHOD AND APPARATUS FOR DETECTING IRREGULARITIES IN TISSUE MICROARRAYS

(75) Inventors: Ali Can, Troy, NY (US); Michael John Gerdes, Albany, NY (US); Xiaodong Tao, Niskayuna, NY (US); Musodiq Olatayo Bello, Niskayuna, NY (US); Maximilian Seel, Boston, MA (US)

(73) Assignee: General Electric Company, Niskayuna, NY (US)

( * ) Notice: Subject to any disclaimer, the term of this patent is extended or adjusted under 35 U.S.C. 154(b) by 1352 days.

(21) Appl. No.: 12/055,038

(22) Filed: Mar. 25, 2008

(65) Prior Publication Data

US 2009/0245610 A1   Oct. 1, 2009

(51) Int. Cl.
G06K 9/36 (2006.01)
G06K 9/62 (2006.01)
(52) U.S. Cl. .................................. 382/133; 382/128
(58) Field of Classification Search ........... 382/128–133
See application file for complete search history.

(56) References Cited

U.S. PATENT DOCUMENTS

| 2003/0039384 | A1* | 2/2003 | Bacus et al. | 382/128 |
| 2003/0231791 | A1* | 12/2003 | Torre-Bueno et al. | 382/133 |
| 2004/0076345 | A1* | 4/2004 | Olszak et al. | 382/309 |
| 2005/0123181 | A1* | 6/2005 | Freund et al. | 382/128 |
| 2006/0014238 | A1* | 1/2006 | Gholap et al. | 435/40.5 |
| 2008/0032328 | A1* | 2/2008 | Cline et al. | 435/40.5 |

OTHER PUBLICATIONS

Rabinovich, et. al. "Framework for Parsing, Visualizing and Scoring Tissue Microarray Images", IEEE Transactions on Information Technology in Biomedicine, vol. 10, No. 2, Apr. 2006, p. 209-219.*
Rabinovich et. al., "Framework for Parsing, Visualizing and Scoring Tissue Microarray Images", IEEE Transactions on Information Technology in Biomedicine, vol. 10 No. 2, Apr. 2006, p. 209-219.*
Rabinovich, et al., "Framework for Parsing, Visualizing and Scoring Tissue Microarray Images", IEEE Transactions on Information Technology in Biomedicine, vol. 10, No. 2, Apr. 2006, p. 209-219.*
Demichelis, et al., "TMABoost: An Integrated System for Comprehensive Management of Tissue Microarray Data", IEEE Transactions on Information Technology in Biomedicine, vol. 10, No. 1, Jan. 2006, p. 19-27.*
A. Rabinovich, S. Krajewski, M. Krajewska, A. Skabaik, S. M. Hewitt, S. Belongie, J. C. Reed, and J. H. Price, "Framework for parsing, visualizing and scoring tissue microarray images," IEEE Trans. on Information Technology in Biomedicine, vol. 10, No. 2, pp. 209-219, 2006.
F. Demichelis, A. Sboner, M. Barbareschi, and R. Dellanna, "TMABoost: An integrated system for comprehensive management of tissue microarray data," IEEE Trans. on Information Technology in Biomedicine, vol. 10, No. 1, pp. 19-27, 2006.
W. Chen, M. Reiss, and D. J. Foran, "A prototype for unsupervised analysis of tissue microarrays for cancer research and diagnostics," IEEE Trans. on Information Technology in Biomedicine, vol. 8, No. 2, pp. 89-96, 2004.
http://biomax.us/faq.php; US Biomax, Inc. FAQs.

* cited by examiner

Primary Examiner — Robert Kim
Assistant Examiner — David E Smith
(74) Attorney, Agent, or Firm — Fletcher Yoder, P.C.

(57) ABSTRACT

The present techniques provide systems and methods for registering images of tissue spots on a tissue microarray (TMA). In studies involving multiple biomarkers being studied on the same TMA, the TMA slide is removed from the microscope, stained, and then imaged, often multiple times. The present techniques relate to validation of the registration of the acquired images of the same TMA. An automatic approach to register the images and detect registration failures as provided herein may enhance the rapid analysis of the tissues. Artifacts such as tissue folding and tissue loss are also determined automatically.

26 Claims, 8 Drawing Sheets

| | A | B | C | D | E | F | G |
|---|---|---|---|---|---|---|---|
| 1 | Row / Column | TMA Number | Image Number | Image Name | Tissue Quality | Registration Quality | Nuclei Count |
| 68 | R05C08 | T14 | 60 | MSKTrial4_T002_S007_E002_P060_DAPI.TIF | GOOD | GOOD | OK |
| 69 | R05C07 | T12 | 61 | MSKTrial4_T002_S007_E002_P061_DAPI.TIF | GOOD | GOOD | OK |
| 70 | R05C06 | N9 | 62 | MSKTrial4_T002_S007_E002_P062_DAPI.TIF | GOOD | GOOD | OK |
| 71 | R05C05 | N7 | 63 | MSKTrial4_T002_S007_E002_P063_DAPI.TIF | GOOD | GOOD | OK |
| 72 | R05C04 | T4 | 64 | MSKTrial4_T002_S007_E002_P064_DAPI.TIF | FOLD | GOOD | FEW |
| 73 | R05C03 | T2 | 65 | MSKTrial4_T002_S007_E002_P065_DAPI.TIF | LOSS | GOOD | OK |
| 74 | R06C03 | T2 | 66 | MSKTrial4_T002_S007_E002_P066_DAPI.TIF | GOOD | GOOD | OK |
| 75 | R06C04 | T4 | 67 | MSKTrial4_T002_S007_E002_P067_DAPI.TIF | GOOD | GOOD | OK |
| 76 | R06C05 | N7 | -1 | | | | |
| 77 | R06C06 | N9 | 68 | MSKTrial4_T002_S007_E002_P068_DAPI.TIF | GOOD | GOOD | OK |
| 78 | R06C07 | T12 | 69 | MSKTrial4_T002_S007_E002_P069_DAPI.TIF | GOOD | GOOD | OK |
| 79 | R06C08 | T14 | -1 | | | | |
| 80 | R06C09 | T18 | 70 | MSKTrial4_T002_S007_E002_P070_DAPI.TIF | GOOD | GOOD | OK |
| 81 | R06C10 | N21 | 71 | MSKTrial4_T002_S007_E002_P071_DAPI.TIF | GOOD | GOOD | FEW |
| 82 | R06C11 | N24 | 72 | MSKTrial4_T002_S007_E002_P072_DAPI.TIF | FOLD | GOOD | OK |

FIG. 2

METHOD AND APPARATUS FOR DETECTING IRREGULARITIES IN TISSUE MICROARRAYS

BACKGROUND

The invention relates generally to image processing and image analysis. More specifically, the present techniques relate to analysis of tissue microarrays.

Tissue microarray (TMA) technology has become the standard in large-scale immunohistochemistry (IHC), fluorescent in situ hybridization (FISH), and mRNA in situ hybridization (RNA-ISH) studies for protein, DNA and RNA expression. To prepare the TMA slides, a tissue core is typically obtained from the patient tissue and inserted in a paraffin recipient block. The resulting recipient block typically has hundreds of tissue cores from multiple patients. This block may then be cut into sections with many different tissue spots corresponding to the tissue cores. The sections may be placed on glass slides for examination and imaging.

The development of TMA technology has generated interest in studies involving multiple biomarkers that may be performed on a single slide, e.g., sequential tissue multiplexing, temporal analysis, change analysis, expression level analysis, and dose analysis. Such studies may allow researchers to investigate complex clinical conditions associated with several different proteins or biomarkers. For certain IHC studies of TMAs, the TMA slide is removed from the microscope after a round of staining and imaging, and bleached to remove the dye that is conjugated with the antibody. The tissue spots on the TMA may then be re-stained with the same dye (or other dyes) that may be conjugated with another antibody targeting different proteins, and the TMA is replaced under the microscope for imaging. This series of staining and bleaching steps on a single TMA may be repeated several times.

Because several images of the same TMA slide are generated from these studies, these images may be registered before further analysis is performed. A bottleneck in automated registration systems is the validation step, which includes the detection and correction of registration failures that may be the result of lost or folded tissue spots on the TMA. This is important because an undetected registration failure may lead to erroneous results in later stages of the automated analysis. In certain types of analysis, such as sequential multiplexing, tools to facilitate validation of the tissue quality in the TMA at each round of staining or bleaching may be advantageous. Tissue quality validation at each step helps to remove damaged tissue from subsequent analysis stages, thus avoiding inaccuracies in biomarker quantitation and tissue scoring. For example, if the registration is not successful for a given step, the protein expression measured at that step may not be correlated with measurement at any other step. Grossly folded or completely lost tissue cores may also influence the accuracy of results. In addition, a tissue core may be neither folded nor lost compared to the baseline state (initial state before any staining or bleaching), but the tissue core selected may have very few cells such that any quantitation will be misleading. Performing this validation for hundreds of tissue cores at each step of a sequentially multiplexed study is highly time-consuming.

Certain techniques for validation of individual tissue spots may involve visual inspection of the combined display of two or more images. For example, this may be accomplished by combining color channels, using two displays with paired cursors, or by using a checkerboard display. One disadvantage with this technique is the time that may be involved with reviewing images of each individual tissue spot. Other techniques provide analysis of an image-to-image metric value. However, this value is highly image-dependent and does not provide information about re-initialization of registration. Another technique involves an analysis of a resulting transformation. This technique is only useful if there is a ground truth to compare with, e.g., when registering to a synthetic image or an atlas. In another technique involving analysis of transformation stability, examining the Jacobian of the transform in the neighborhood of the transform returned by the registration method may be used. However, this approach does not preclude the selection of a local minimum, and does not suggest re-initialization values.

BRIEF DESCRIPTION

The present techniques provide automated tools for tissue quality assessment of individual tissue spots in a TMA. To facilitate efficient verification, multi-channel thumbnail versions of all images on a TMA may be presented to the user as laid out on the TMA slide. Each thumbnail is a composite image of the image being evaluated and the corresponding baseline image before any sequential step. Tissue folding and loss may be evaluated in these thumbnails. The thumbnails may be further annotated, with color indicators or otherwise, with the status of the tissue quality, registration quality, and tissue viability. Any inaccuracy may be corrected in an accompanying spreadsheet. The spreadsheet may serve as input to any automated image analysis process or to manual scoring.

In certain embodiments, the present techniques involve comparing an image of each tissue spot at a given step with a corresponding baseline tissue image. By applying thresholds on an image-to-image metric, tissue spots with partial tissue folding or substantial tissue loss are identified.

The present techniques also provide tools for tissue viability assessment. In certain embodiments, the present techniques identify tissue spots that have an insufficient number of cells for analysis. Once identified, these spots may be excluded from further analysis (e.g., protein expression analysis, predictive or correlation studies for cancer, biomarker discovery, pharmaceutical applications, etc.). In certain embodiments, such spots may be identified by counting the nuclei (and/or cells) present in the spot.

The present techniques also provide tools for registration status assessment. Using an image-independent registration failure detection algorithm, the present techniques may identify images where registration has failed, identifying these cases as candidates for re-registration or for exclusion from further analysis.

The present techniques also provide tools for absolute position indication of tissue spots. In certain embodiments, the present techniques use the relative positions of the tissue spots on the slide to determine the correct row and column position of each TMA tissue spot. These coordinates are useful for matching TMAs in different serial sections and for directly relating with the TMA-map as well as clinical information.

In certain embodiments, the present techniques may have any suitable output. For example, the output may be a spreadsheet file that shows the registration status, tissue quality, tissue viability, absolute coordinates, and/or image number of each tissue spot. The generated spreadsheet may allow user input to verify or reject any of the assessments. The present techniques are also adapted to output an annotated whole slide. All the tissue spots on a TMA may be presented for viewing at once as laid out on the slide, with each image annotated with its quality metrics. This translates to two orders of magnitude in productivity compared to viewing each image individually.

The present techniques provide a method for analyzing a tissue microarray, that includes accessing two or more images of a tissue microarray that includes a plurality of tissue spots; registering corresponding tissue spots on the two or more images; determining the quality of each of the plurality of tissue spots; and generating an output indicating the registration quality of the plurality of spots between the two or more images and the quality of the plurality of tissue spots in at least one of the two or more images.

The present techniques provide a computer-readable medium that includes instructions for: accessing two or more images of a tissue microarray comprising a plurality of tissue spots; registering corresponding tissue spots on the two or more images; determining the quality of each of the plurality of tissue spots; and generating an output indicating the registration quality of the plurality of spots between the two or more images and the quality of the plurality of tissue spots in at least one of the two or more images.

The present techniques provide an image analysis system that includes: a processor adapted to access two or more images of a tissue microarray comprising a plurality of tissue spots. The processor is adapted to run instructions for: registering corresponding tissue spots on the two or more images; determining the quality of each of the plurality of tissue spots; and generating an output indicating the registration quality of the plurality of spots between the two or more images and the quality of the plurality of tissue spots in at least one of the two or more images.

The present techniques provide an image overview of a tissue microarray that includes: images of each of a plurality of tissue spots on the tissue microarray; a tissue quality indicator associated with each of the tissue spots; and a registration indicator associated with each of the tissue spots.

DRAWINGS

These and other features, aspects, and advantages of the present invention will become better understood when the following detailed description is read with reference to the accompanying drawings in which like characters represent like parts throughout the drawings, wherein:

FIG. 2 is an exemplary spreadsheet output format in accordance with aspects of the present technique;

DETAILED DESCRIPTION

The present techniques provide automated systems and methods for registering images of corresponding tissue spots in a TMA, detecting cases of registration failures, and/or re-initializing registration in the case of registration failure. The present techniques may reduce the incidence of individual validation of each tissue spot on a TMA. By providing a whole TMA image output, any tissue spot that failed to register may be annotated with a flag or other indicator. This output may allow an operator to scan an entire slide and quickly identify those tissue spots that may warrant additional validation and/or exclusion from further analysis.

Figure 1:
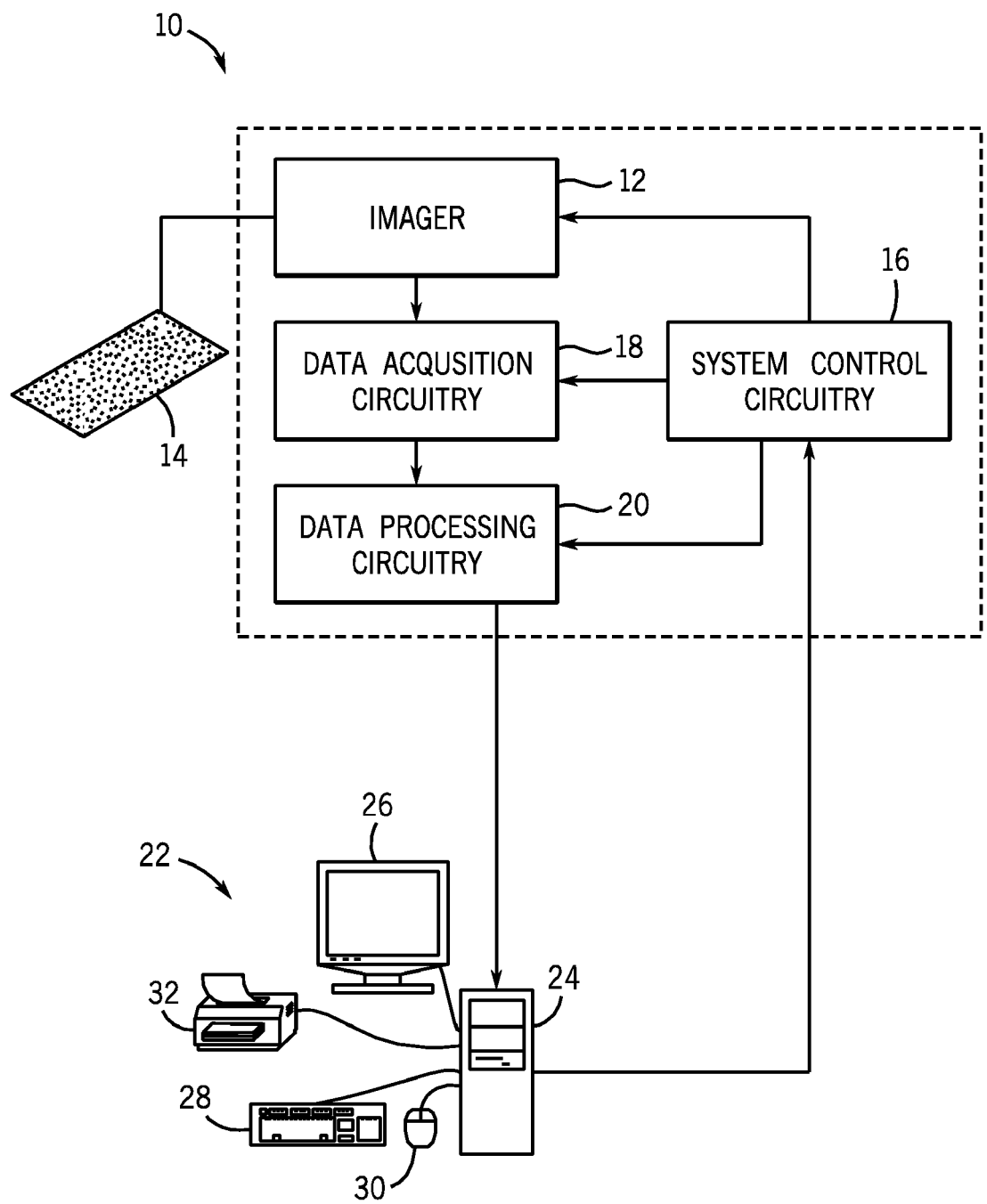
FIG. 1 is a diagrammatical view of an exemplary system for use in acquiring image data of TMAs in accordance with aspects of the present technique.

The present techniques may use images of the tissue spots on a TMA and the relative x-y coordinates of each tissue spot as recorded by a microscope or other suitable image acquisition system. In certain embodiments, it is envisioned that the present techniques may be used in conjunction with previously acquired images, for example, digitally stored images, in retrospective studies. In other embodiments, the images may be acquired from a physical sample. In such embodiments, the present techniques may be used in conjunction with an image acquisition system. An exemplary imaging system 10 capable of operating in accordance with the present technique is depicted in FIG. 1. Generally, the imaging system 10 includes an imager 12 that detects signals and converts the signals to data that may be processed by downstream processors. The imager 12 may operate in accordance with various physical principles for creating the image data and may include a fluorescent microscope, a bright field microscope, or devices adapted for suitable imaging modalities. In general, however, the imager 12 creates image data indicative of a biological sample including a population of cells 14, shown here as being multiple samples on a tissue micro array. The image may be a digital image or a film image. As used herein, the term "biological material" or "biological sample" refers to material obtained from, or located in, a biological subject, including biological tissue or fluid obtained from a subject. Such samples may be, but are not limited to, body fluid (e.g., blood, blood plasma, serum, or urine), tissues, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, a population of cells from a biological fluid (e.g., blood or urine).

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic, electronic, or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquired image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple wells of a multi-well plate). The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the computer 24 may include various memory and/or storage components including magnetic and optical mass storage devices and/or internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage medium and/or memory remote from the operator workstation 22 but accessible by network and/or communication interfaces present on the computer 24.

The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging system or station may include an operator workstation 22 which permits regulation of the parameters involved in the image data acquisition procedure, whereas a different operator workstation 22 may be provided for manipulating, enhancing, and viewing results and reconstructed images.

The present techniques provide validation of images of TMAs, such as those acquired by the system of FIG. 1, presented in a variety of outputs. In one embodiment, shown in FIG. 2, a spreadsheet may be produced with a summary of validation data for a specific TMA or TMAs. For example, the spreadsheet may include information for each tissue spot on the TMA, such as a corresponding row in the spreadsheet with information about the absolute position of the spot on the TMA slide. The absolute position may be expressed as row and column indices and/or the corresponding number in the TMA map for the recipient block. In certain embodiments, these positions may be used to relate a spot to the corresponding spot in other TMAs as well as to clinical information. Such clinical information may include, for example, patient identification information, patient identification numbers, diagnosis information, treatment information, medical history information, biochemical information, physiologic information, family history information, patient dietary information, patient exercise information, demographic information, or drug response information. The clinical information also may include genotype information or haplotype information, such as a chromosome structure, a DNA sequence, a length of a specific gene or region, a gene expression, or at least one single nucleotide polymorphism (SNP). In another embodiment, the clinical information may include information related to one or more clinical trials. In one embodiment, the clinical information may include information related to the tissue core, such as tissue type, pathological information, and information about the preparation and storage procedures related to the tissue core. The spreadsheet may also include the serial number of the image in that spot. In certain embodiments, this number may be set to −1, or any other alphanumeric flag value, if the spot is blank (e.g., if the tissue core fell off). Image registration quality, tissue quality compared to the baseline (good tissue/partial tissue folding/substantial tissue loss), tissue core viability (based on nuclei count) may also be generated automatically for the tissue core and included in each row. In addition, there may be a comment column for the user to note any changes that are made to the spreadsheet during manual verification. This spreadsheet may serve as input to the next stages of tissue scoring.

Figure 3A:
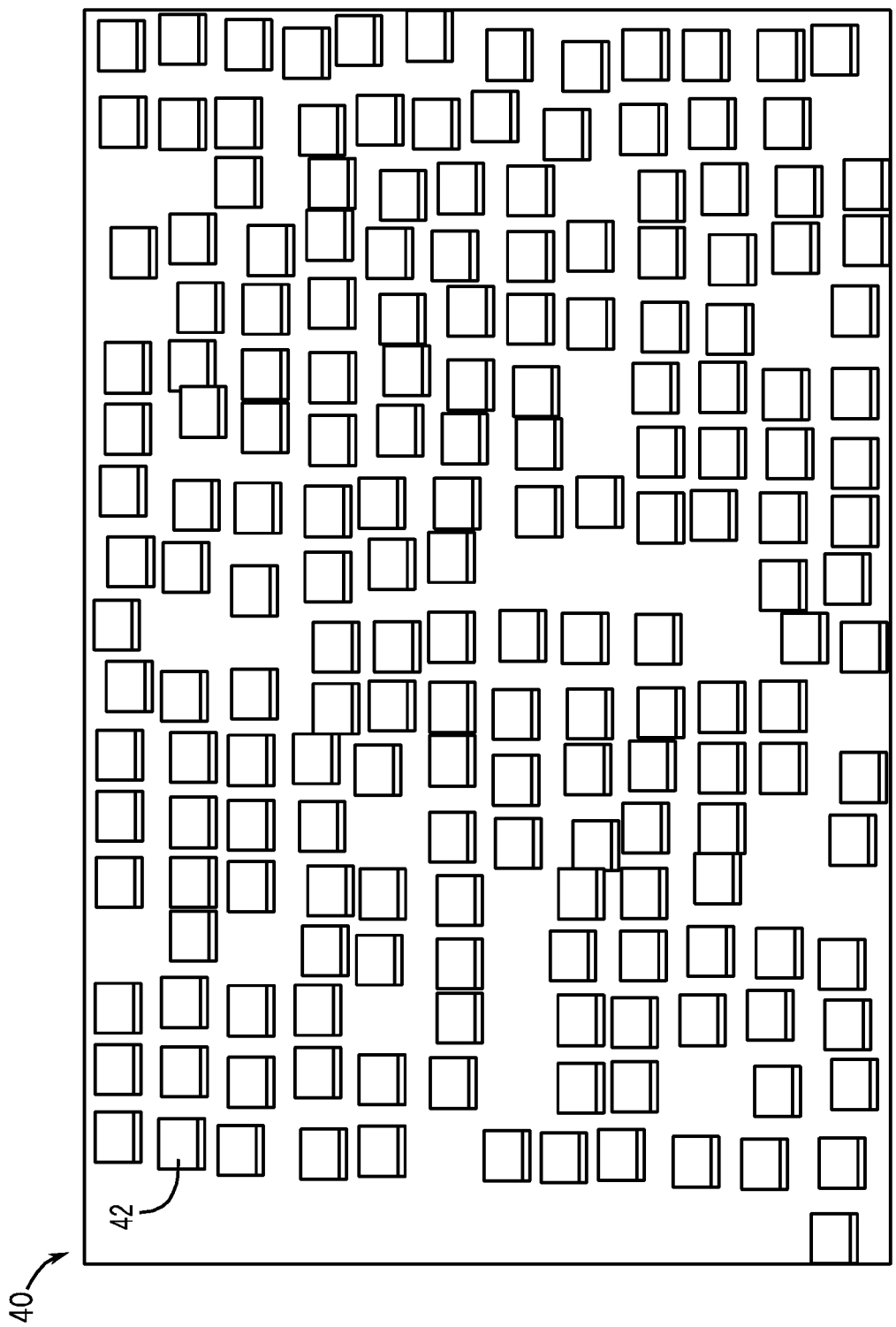
FIG. 3A is an exemplary TMA image overview output format in accordance with aspects of the present technique.
Figure 3B:
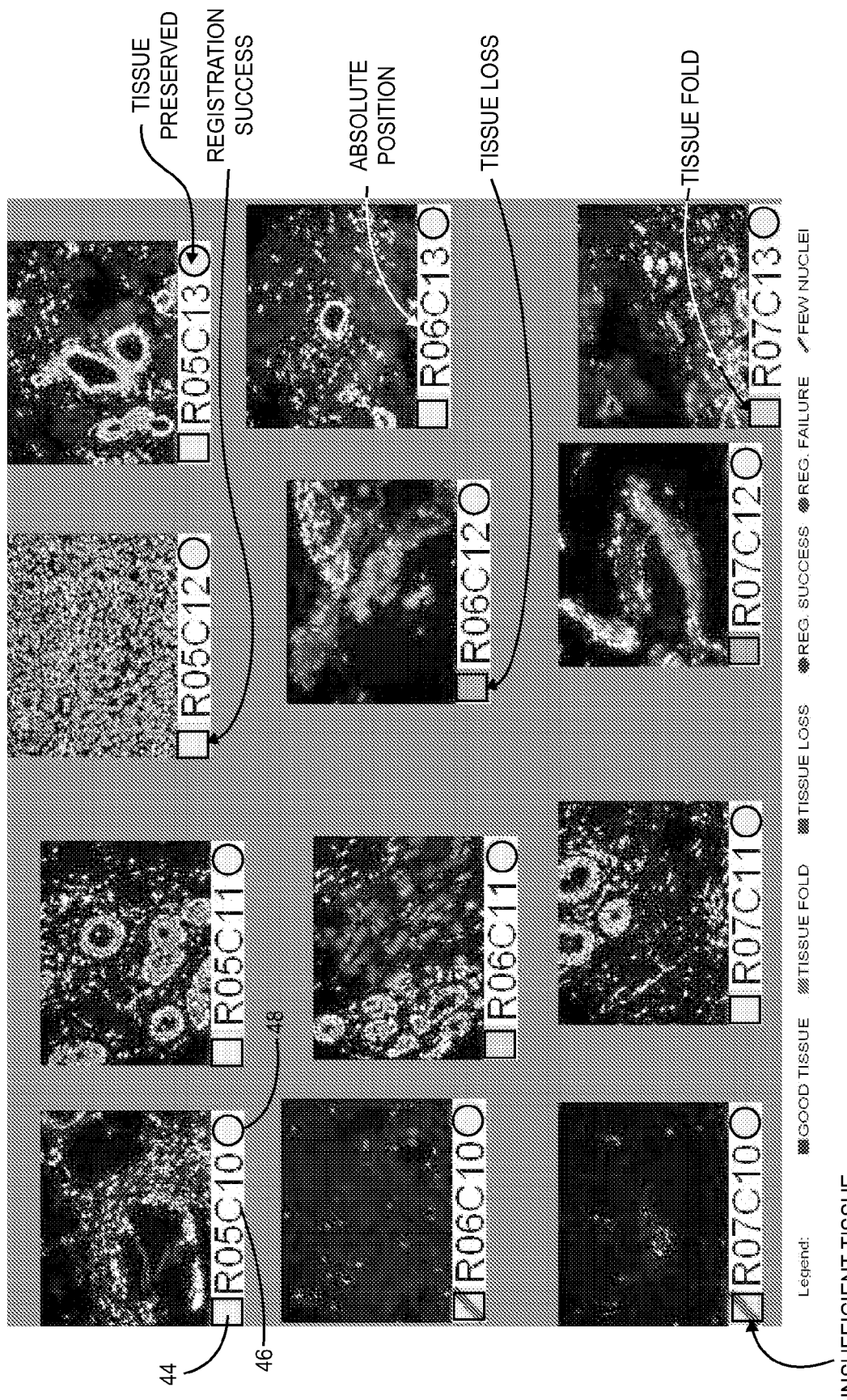
FIG. 3B is an exploded view of a portion of the image overview of FIG. 3A.

FIG. 3A depicts the slide overview 40 for a typical step and FIG. 3B illustrates typical annotations on each thumbnail. A user may quickly use this slide overview image 40 to verify the spreadsheet output. This overview image 40 may be viewed in any image viewer and is intended for use in validating the generated spreadsheet. By comparing the thumbnail display 42 of each tissue spot with the annotation associated with each thumbnail 42, a user may easily verify the automated annotations and modify the spreadsheet as appropriate. This slide overview 40 may be a JPEG image that has a thumbnail image 42 of each tissue spot arranged according to the location of the cores in the actual TMA slide. These locations may be obtained from the microscope during imaging. As shown in FIG. 3B, each thumbnail 42 may have a status bar that indicates the registration quality 48, tissue quality or tissue usability 44, and absolute position 46. For example, as shown, the tissue quality or usability indicator 44 may be a square or other suitable symbol. In certain embodiments, the square may be colored, such as with green, orange, or red to indicate good, partial folding, or tissue loss respectively. In such embodiments, a line across the tissue quality indicator 44 (irrespective of the quality) may be used to indicate that the tissue core is not viable based on the presence of very few nuclei. Further, in other embodiments, a registration quality indicator 48 may be a circle on the right of the status bar. In such embodiments, the registration quality indicator 48 may be colored green or red to indicate the status of the registration success or failure respectively. Additionally, the absolute position indicator 46 may include row and column numbers as well as information about which section from a particular recipient block was imaged.

In certain embodiments (not shown), the overview image 40 may be viewed in a web browser where each thumbnail image 42 has hyperlinks to the original image being evaluated as well as the corresponding baseline image. This allows the user to quickly view the full resolution image data with a single click from the TMA slide overview 40.

Figure 4:
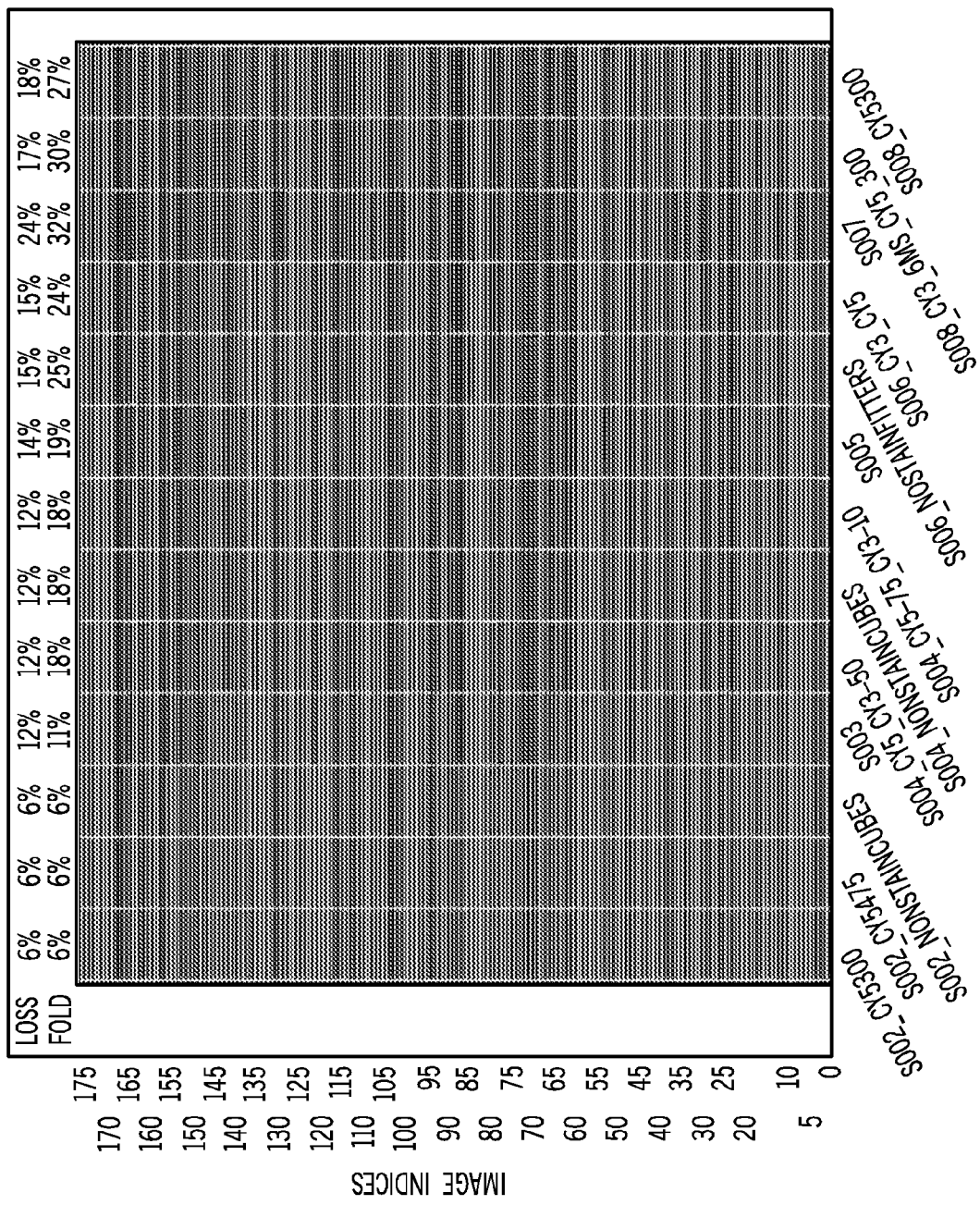
FIG. 4 is an exemplary chart output format illustrating the tissue quality in accordance with aspects of the present technique.

In certain embodiments, the present techniques may also provide a validation output, such as a plot 50, shown in FIG. 4, summarizing the tissue status across a number of steps in a multi-step study. This makes it easy to compare the tissue quality across multiple sequential steps at a glance. Such a plot 40 may take the form where each row represents a tissue spot and each column represent a sequential step. For example, each sequential step could be staining with a different dye and/or antibody, which may be indicated in the x-axis legend 52. Bars 54 of a certain color (green for good quality, red for tissue loss, and orange for folded or partially folded tissue) may allow a user to quickly scan hundreds of bars, each representing a tissue spot on a TMA image taken at one step of a multi-step process. The percentage of folded and lost tissues may be indicated in a legend 56 at the top of each column.

With the forgoing in mind, the following relates to additional embodiments of the present techniques. In certain embodiments, images taken of a single TMA at different times may be normalized for the illumination pattern before comparing them. The illumination pattern may be estimated from the images, or directly computed by using calibration targets. Most filter-cube and microscope manufacturers provide fluorescent plastics that may be used for calibration. If the calibration images are not taken during the acquisition, or the illumination changed during maintenance, the illumination pattern may be estimated from a series of images.

For example, the observed image, I(x, y), may be modeled as a product of the excitation pattern, E(x, y), and the emission pattern, M(x, y). While the emission pattern captures the tissue dependent staining, the excitation pattern captures the illumination pattern:

$$I(x,y)=E(x,y)M(x,y). \quad (1)$$

In the logarithm domain, the above equation may be transformed to a linear form:

$$\log(I(x,y))=\log(E(x,y))+\log(M(x,y)). \quad (2)$$

From a set of N images, let $I_n(x, y)$ denote an ordered set of pixels. In other words, for any given (x, y) location the pixels are sorted such that $$I_1(x,y) \leq I_2(x,y) \leq \ldots I_n(x,y) \ldots \leq I_N(x,y) \quad (3)$$

Assuming that a certain percentage (p) of the image is formed from stained tissue (non-zero background), then a trimmed average of brightest pixels may be used to estimate the log of the excitation pattern:

$$E'_{AVE}(x, y) = \frac{1}{N - K + 1} \sum_{n=K}^{N} \log(I_n(x, y)), \quad (4)$$

where K is set to an integer closest to N(1−p)+1. In certain embodiments, p may be set to 0.1 (10%). In the above equation the average emission pattern of the tissue is assumed to be uniform across the image. Since the images may be recovered up to a scale factor, the constant term introduced by the uniform emission pattern may be dropped. This approximation holds if large number of images are used in the averaging process. However a large percentage of pixels (90%) are already excluded to eliminate the non-tissue pixels in the images. To overcome the limited sampling size, it may be advantageous to approximate the log of the excitation pattern with polynomials:

$$E'_{AVE}(x, y) = \sum_{0 \leq i, j \leq p; i+j \leq p} a_{ij} x^i y^j. \quad (5)$$

Figure 5B:
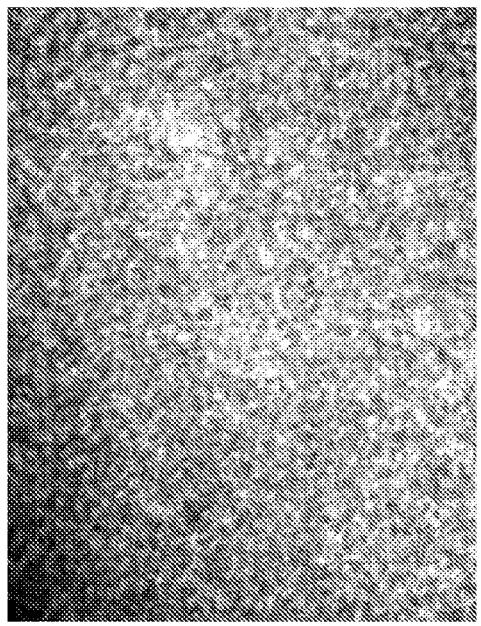
FIG. 5B is an estimated excitation pattern of a baseline image in the ninth step of an exemplary multi-step study in accordance with aspects of the present technique.
Figure 5D:
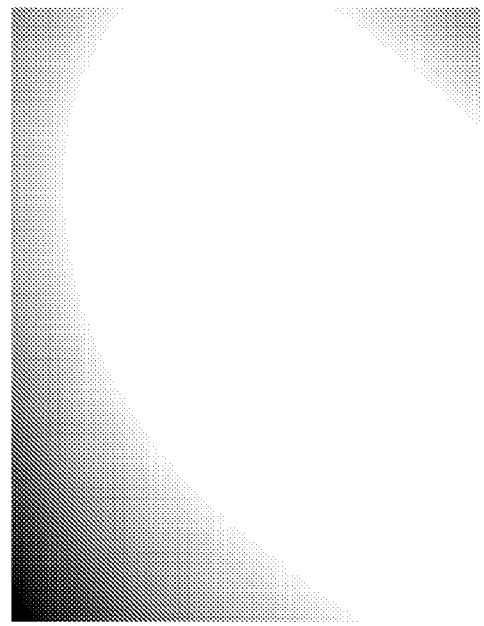
FIG. 5D is an estimated third order polynomial surface for the image of FIG. 5B in accordance with aspects of the present technique.
Figure 5A:
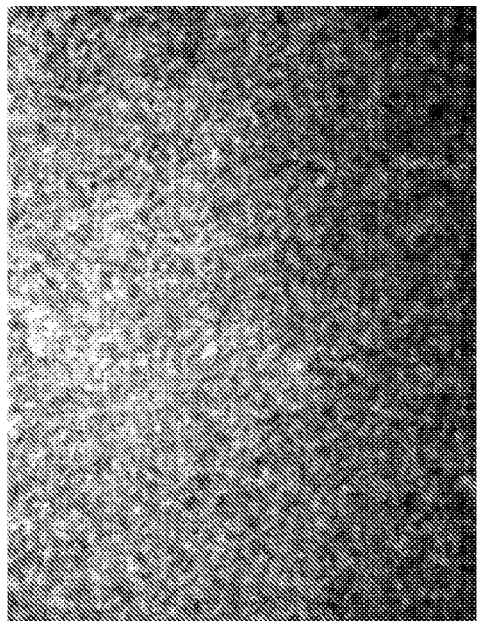
FIG. 5A is an estimated excitation pattern of a baseline image in the first step of an exemplary multi-step study in accordance with aspects of the present technique.
Figure 5C:
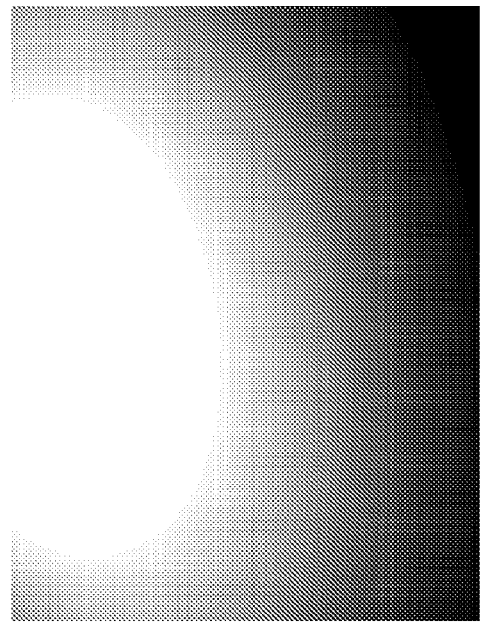
FIG. 5C is an estimated third order polynomial surface for the image of FIG. 5A in accordance with aspects of the present technique.

The parameters $a_{ij}$ are solved by minimizing mean squared error. The surface generated by the polynomial coefficients is then used to correct individual images. Sample excitation patterns and the corresponding estimated polynomial illumination surfaces for two steps in the sequential multiplexing study are shown in FIGS. 5A and B. FIG. 5A shows the excitation pattern of a baseline image in the first step of a sequential multiplexing study. FIG. 5B shows the excitation pattern of a baseline image in the ninth step of a sequential multiplexing study. As evidenced by FIGS. 5A and 5B, the excitation pattern has shifted after nine steps of processing. Where only the brightest 10% of pixels are used to estimate the mean excitation pattern, FIG. 5C is the estimated third order polynomial surface for the image of FIG. 5A and FIG. 5D is the estimated third order polynomial surface for the image of FIG. 5B. When a composite RGB image was made from two images by using one image as the red channel, the other image as the blue channel, and the average of the two images as the green channel, the corrected composite RGB image resembled a grayscale image without any substantial color bias. The uncorrected RGB image may include residual color tones.

Additional embodiments include the generation of multi-channel thumbnail images 42. Each thumbnail image 42, for example, may include two downsampled DAPI images, an image of interest and a baseline image. In one embodiment the baseline image is the first step of the sequential staining steps. The image of interest is put in the blue channel of an RGB image, the corresponding baseline image in the red channel, and the mean of both images put in the green channel for better visualization. With this multi-channel image, in certain embodiments, good tissue appears white, lost tissue appears red (since it is present in the baseline tissue but not in the step being analyzed) and folded tissue appears as a non-uniform mixture of red, blue and orange. Registration failures may appear as misaligned red and blue images. During validation, a user may see all the images on a TMA in the overview image 40 at a glance and correlate with the automatic annotation on the status bar. If the user disagrees with the automatic annotation, the spreadsheet may be easily edited to reflect the user assessment. The size of the thumbnails is user-configurable, and may be adjusted to accommodate the screen size of the user and the amount of details required. The thumbnails are arranged in the same layout on the slide as captured by the microscope, making it easy to identify missing spots.

As noted, studies such as sequential multiplexing involve comparing the same tissue sample, and resulting images, in different sequential steps. For this to be achieved automatically, the images may be co-registered so that comparison may then be made at the sub-cellular (or even pixel) level. The present techniques utilize an algorithm that automatically identifies tissue cores with failed registration when compared to other cores on the TMA. The algorithm gives a quantitative estimate of the extent of mis-registration by applying a predetermined threshold for labeling tissue core images. The present techniques are independent of tissue type or image modality and may be applied to the tissue spots located on the same slide if the coordinates of the spots are known. For example, the coordinates may easily be obtained from the imaging microscope or from raw image data of a TMA.

Figure 6:
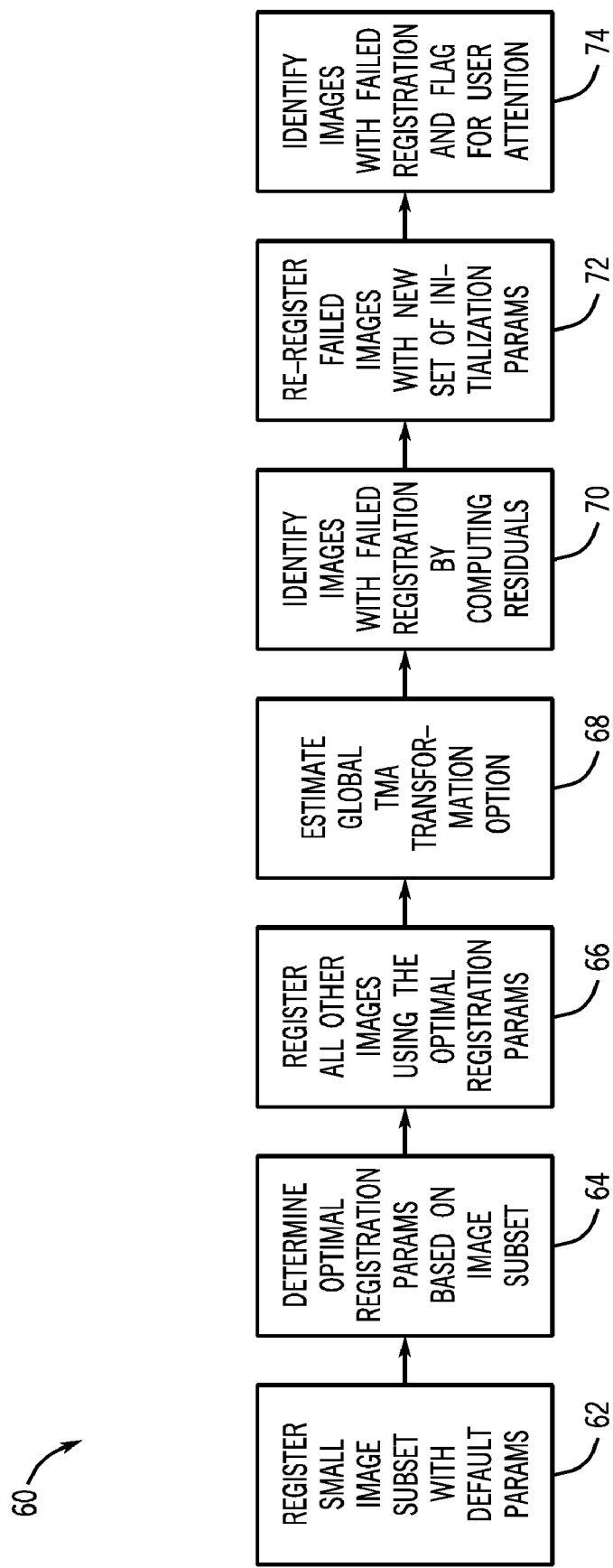
FIG. 6 is a flowchart of a method of registering images in accordance with the present technique.

Exemplary steps in a registration failure process 60 are depicted in system are depicted in FIG. 6. Step 62 involves registration of a small subset of images. All images in the small subset are registered initially using default registration parameters. In an exemplary embodiment, to establish ground truth transformations for images in this subset, the registration performance may be visually verified and cases of registration failures are manually re-initialized until the registration succeeds. The purpose of this step is to quickly explore the registration parameter space. In certain embodiments, step 62 as well as step 64 may be skipped if the default parameters are known to be reliable for the application domain. The number of images in this exploratory subset may be quite small. In step 64, estimation of optimal registration parameters is performed using a Design of Experiments approach as provided herein. Different combinations of parameters are used to register the images in the exploratory image subset and the performance compared with the ground truth. The parameter combination that gives the highest accuracy is selected as the optimal registration parameters.

Step 66 involves registration of all other images with the optimal parameters. It should be noted that in certain embodiments, the labor-intensive first and second steps may be done only once for a given instrumentation, incorporating variations in stage, optics, and camera systems. For subsequent TMA analysis, the same optimal parameters may be used. The user may start their DOE around the optimal parameters suggested in Table 1 (below). Step 68 involves an estimation of the global TMA transformation parameters. The global transformation parameters provide information about the misalignment of the TMA slide, and contribute to the transformation parameters of each image on the TMA. Step 70 involves the detection of registration failure. In step 72, the algorithm performs registration of failed cases with new parameters. All images where the registration failed are re-registered using new initialization values computed from both the global transformation values and the coordinates of each image on the TMA. Additionally, in step 72, cases of repeated registration failure are flagged. The re-registered images are assessed again for registration failures. Cases of failures are then identified for user intervention.

Registration corrects for global and local transformations. The global transformation for each staining round is due to positioning the TMA in a different location under the microscope after each round of staining. Local transformation for each image may be due to the stage inaccuracy in the microscope system. However, if a highly accurate microscopy system may be employed, the local transformations may be relatively small compared to the global transformation. It is important to note that registration accuracy is affected mainly by (i) the type of image registration metric, (ii) the registration parameters, and (iii) the initialization. Metrics commonly used for registration include mean-squared difference, mutual information, and normalized correlation. Registration parameters include optimizer parameters (such as the step length and relative scales of each transformation parameter) and image metric parameters (such as the number of samples to use from the image and the number of histogram bins to split the intensity range into). If the transformation between the image to be registered (i.e., moving image) and the reference (i.e., fixed) image is large, setting a good initial value for the transformation increases the chances of success for the registration.

In certain embodiments, in step 66, a rigid registration may be employed to align individual images in the TMA. Rigid registration may be sufficient since any misalignment may be accounted for with a rotation and a translation. In an exemplary embodiment in which registration was performed on TMA images, each image i was registered in two image resolution levels to ensure robustness. At the first level, both the fixed and moving images were scaled to 25% of the original size, and smoothed with a recursive Gaussian kernel ($\sigma$=36). An identity transform, with both the initial rotation and translation set to 0, was used to initialize this level. In this implementation, the relatively high subsampling and smoothing allowed fast convergence of the registration in most cases. The resulting transformation values (rotation $r_i$ and translation $t_i$) obtained from the first level were then used to initialize the second round of registration on the full image also smoothed with a Gaussian kernel ($\sigma$=9). Matte's Mutual Information metric and a regular-step gradient descent optimizer were used in both steps.

In image registration terms, Mutual Information (MI) measures how much information the intensity in one image informs about the intensity in another. MI is robust to differences in intensity values between the two images and is therefore well suited in sequential staining where the fluorescence may become weaker in progressive rounds of staining. MI is defined in terms of entropy. Given two images A and B, the entropy in the images are computed as:

$$H(A)=-\Sigma p_A(a)\log p_A(a) \text{ and } H(B)=-\Sigma p_B(b)\log p_B(b), \quad (6)$$

where $p_A(a)$ denotes the probability that a random pixel in image A has a value a. The joint entropy of the images is represented as $$H(A, B) = -\sum_A \sum_B p_{AB}(a, b)\log p_{AB}(a, b). \quad (7)$$

The Mutual Information, MI(A, B), between the two images is computed as $$MI(A,B)=H(A)+H(B)-H(A,B). \quad (8)$$

In certain embodiments, one set of intensity samples is drawn from each of the images and the marginal and joint probability density function (PDF) is evaluated at discrete positions or bins uniformly spread within the dynamic range of the images. Entropy values are computed by summing over the bins. Prior normalization of the images may not be employed as the MI metric rescales internally when building up the discrete density functions.

Using the MI metric, the user-defined registration parameters may include number of samples, number of bins, rotation scale, and maximum step length. The number of samples is the number of pixel samples used in the fixed and moving images to compute the density estimate. Taking too few samples may result in a poor representation of the images, which in turn increases the likelihood of registration failure. On the other hand, a large number of samples increases the computational requirements and slows down the algorithm. As a rule of thumb, about 1% of the pixels is sufficient if the images are smooth and do not contain much detail, but up to 20% may be required if the images are detailed. The number of bins used to compute the entropy may also be user-defined. Rather than computing the probability that a pixel has a particular intensity value in Equation 6, the probability that the pixel belongs to a particular histogram bin is computed. The range of intensity values is uniformly distributed over the number of bins. Since the units of the angle of rotation θ and translations $t_x$ and $t_y$ are different, the parameters may be scaled before evaluation by the optimizer. The step length is the jump made by the optimizer in parametric space at each iteration of the registration process. Starting from a user specified maximum, the optimizer progressively reduces the step length whenever a change of direction is detected in parametric space. This allows for smooth convergence. Setting the maximum to a large value may result in large jumps, skipping over the global minima. If it is too small, the optimizer may require too many iterations or may never reach the minima.

In one implementation, after registering the images in step 66 above, each registered moving image was overlaid with the fixed image to visually verify correct registration. In the cases where the registration failed, the initialization was manually adjusted and the parameters for the MI metric were manually tuned until the images were correctly registered. The transformation values of these visually validated registered images were then taken as the ground truth. The performance of a set of registration parameters may be assessed by comparing the resulting transformation parameters with the ground truth transformation values. This comparison is performed by computing the average Euclidean distance between a set of uniformly sampled grid points warped with the ground truth values and the same points warped with the newly computed transformation values. For example, let $P=\{P_{(1)}, P_{(2)}, \ldots, P_{(n)}\}$ be a set of n uniformly sampled points in image coordinates. Also, let $P_g\{P_{g(1)}, P_{g(2)}, \ldots, P_{g(n)}\}$ be the same set of points after transforming with ground truth transformation $T_g$, and let $P_r=\{P_{r(1)}, P_{r(2)}, \ldots, P_{r(n)}\}$ represent the points when transformed with another transformation $T_r$. The warping differential between the two transformations is computed as $$W_{(g,r)} = \frac{1}{n}\sum_{i=1}^{n}\sqrt{(P_{g(i)} - P_{r(i)})^2} . \quad (9)$$

A threshold may be set such that a value of W greater than the threshold indicates a large difference between the two transformations, which in turn implies that the registration represented by the transformation values $T_r$ is a failure with respect to the ground truth. Based on the experiments, correct registrations usually have W very close to zero, and a threshold of 10 captures all failed registrations. The transformations may similarly be compared using distances in the Riemannian space of 2D rigid transforms.

After establishing the ground truth transformation parameters, the set of registration parameters optimal for registering all the images may be estimated in step 68. In one embodiment, this was determined by using a full factorial Design of Experiments (DOE). The transformation parameters obtained with each registration was compared with the ground truth parameters by comparing the warping of a regular grid. The accuracy obtained using different combination of registration parameters are presented in Tables 1 and 2. In the tables, Set 1 refers to the good tissues, and Set 2 refers to partially damaged tissues. The parameters used in the described experiments were from Run 18, below in Table 1, which gave 99.81% overall registration accuracy (compared with the validated ground truth values). These parameters were used to register all the images in an exemplary embodiment.

TABLE 1

Accuracy obtained in DOE runs as multiple registration parameters are varied (Step length = 2).

| Run | Number Of Bins | Maximum Step Length | Rotation Scale | Number Of Samples | Accuracy (Set 1) | Accuracy (Set 2) | Accuracy (Overall) |
|---|---|---|---|---|---|---|---|
| Run01 | 20 | 2 | 10 | 5000 | 93.47% | 88.44% | 93.32% |
| Run02 | 20 | 2 | 1000 | 5000 | 99.81% | 96.44% | 99.61% |
| Run03 | 20 | 2 | 1000000 | 5000 | 99.88% | 96.89% | 99.66% |
| Run04 | 20 | 2 | 10 | 50000 | 94.85% | 92% | 94.84% |
| Run05 | 20 | 2 | 1000 | 50000 | 99.81% | 96.44% | 99.61% |
| Run06 | 20 | 2 | 1000000 | 50000 | 99.88% | 96% | 99.56% |
| Run07 | 20 | 2 | 10 | 100000 | 94.23% | 89.78% | 94.11% |
| Run08 | 20 | 2 | 1000 | 100000 | 99.81% | 96.44% | 99.61% |
| Run09 | 20 | 2 | 1000000 | 100000 | 99.88% | 96.89% | 99.66% |
| Run10 | 50 | 2 | 10 | 5000 | 88.39% | 74.67% | 87.77% |
| Run11 | 50 | 2 | 1000 | 5000 | 99.50% | 88.89% | 98.54% |
| Run12 | 50 | 2 | 1000000 | 5000 | 99.50% | 88.89% | 98.49% |
| Run13 | 50 | 2 | 10 | 50000 | 93.98% | 91.56% | 94.20% |
| Run14 | 50 | 2 | 1000 | 50000 | 99.75% | 96.89% | 99.61% |
| Run15 | 50 | 2 | 1000000 | 50000 | 99.81% | 96.89% | 99.66% |
| Run16 | 50 | 2 | 10 | 100000 | 94.78% | 92.89% | 94.69% |
| Run17 | 50 | 2 | 1000 | 100000 | 99.81% | 96.89% | 99.66% |
| Run18 | 50 | 2 | 1000000 | 100000 | 99.88% | 97.33% | 99.71% |
| Run19 | 125 | 2 | 10 | 5000 | 77.41% | 41.78% | 74.09% |
| Run20 | 125 | 2 | 1000 | 5000 | 90.32% | 56% | 87.73% |
| Run21 | 125 | 2 | 1000000 | 5000 | 90.38% | 54.22% | 87.54% |
| Run22 | 125 | 2 | 10 | 50000 | 90.25% | 76% | 89.13% |
| Run23 | 125 | 2 | 1000 | 50000 | 99.63% | 88.89% | 98.64% |
| Run24 | 125 | 2 | 1000000 | 50000 | 99.63% | 90.67% | 98.78% |
| Run25 | 125 | 2 | 10 | 100000 | 91.99% | 80.89% | 91.13% |
| Run26 | 125 | 2 | 1000 | 100000 | 99.63% | 93.33% | 99.12% |
| Run27 | 125 | 2 | 1000000 | 100000 | 99.63% | 92.89% | 99.03% |

TABLE 2

Accuracy obtained in DOE runs as multiple registration parameters are varied (Step length = 5).

| Run | Number Of Bins | Maximum Step Length | Rotation Scale | Number Of Samples | Accuracy (Set 1) | Accuracy (Set 2) | Accuracy (Overall) |
|---|---|---|---|---|---|---|---|
| Run01 | 20 | 5 | 10 | 5000 | 91.24% | 84% | 90.89% |
| Run02 | 20 | 5 | 1000 | 5000 | 99.81% | 96.44% | 99.78% |
| Run03 | 20 | 5 | 1000000 | 5000 | 99.88% | 96.89% | 99.78% |
| Run04 | 20 | 5 | 10 | 50000 | 93.29% | 88.44% | 93.21% |
| Run05 | 20 | 5 | 1000 | 50000 | 99.81% | 95.11% | 99.62% |
| Run06 | 20 | 5 | 1000000 | 50000 | 99.88% | 96% | 99.67% |
| Run07 | 20 | 5 | 10 | 100000 | 93.18% | 90.67% | 93.33% |
| Run08 | 20 | 5 | 1000 | 100000 | 99.81% | 96.44% | 99.78% |
| Run09 | 20 | 5 | 1000000 | 100000 | 99.88% | 96.89% | 99.78% |
| Run10 | 50 | 5 | 10 | 5000 | 85.89% | 68% | 84.90% |
| Run11 | 50 | 5 | 1000 | 5000 | 99.50% | 90.22% | 98.81% |
| Run12 | 50 | 5 | 1000000 | 5000 | 99.63% | 90.67% | 98.86% |
| Run13 | 50 | 5 | 10 | 50000 | 91.72% | 87.95% | 91.62% |
| Run14 | 50 | 5 | 1000 | 50000 | 99.75% | 96.44% | 99.84% |
| Run15 | 50 | 5 | 1000000 | 50000 | 99.88% | 97.33% | 99.84% |
| Run16 | 50 | 5 | 10 | 100000 | 93.10% | 86.67% | 92.67% |
| Run17 | 50 | 5 | 1000 | 100000 | 99.81% | 97.33% | 99.84% |
| Run18 | 50 | 5 | 1000000 | 100000 | 99.88% | 97.33% | 99.84% |
| Run19 | 125 | 5 | 10 | 5000 | 70.25% | 40.89% | 68.42% |
| Run20 | 125 | 5 | 1000 | 5000 | 94.98% | 66.22% | 92.74% |
| Run21 | 125 | 5 | 1000000 | 5000 | 94.48% | 66.22% | 92.20% |
| Run22 | 125 | 5 | 10 | 50000 | 87.63% | 70.98% | 86.37% |
| Run23 | 125 | 5 | 1000 | 50000 | 99.69% | 92.44% | 99.24% |
| Run24 | 125 | 5 | 1000000 | 50000 | 99.75% | 91.56% | 99.13% |
| Run25 | 125 | 5 | 10 | 100000 | 88.71% | 83.11% | 88.35% |
| Run26 | 125 | 5 | 1000 | 100000 | 99.75% | 95.11% | 99.62% |
| Run27 | 125 | 5 | 1000000 | 100000 | 99.81% | 93.78% | 99.40% |

To automatically determine registration failures, the present techniques rely upon two key concepts: First, all the images are affected by the same global transformation since they are co-located on the same TMA slide, and the relative position of the spots do not change in-between image acquisition rounds. Second, most of the images in the TMA are correctly registered (i.e., registration failures are few). This is a reasonable assumption following the rigorous procedure to obtain the registration parameters.

Registration as described herein was performed on individual images in local image coordinate space to obtain parameters of a rigid transformation: the rotation angle θ about the origin (top left corner of image) and two translations in the x and y directions ($t_i = [t_x, t_y]_i^T$). In certain embodiments, the coordinates of a point in an image are $x_i = [x_i, y_i]^T$ and the coordinates of the same point after registration to the reference (fixed) image are $x_{i'} = [x_{i'}, y_{i'}]^T$. The registered coordinates $x_{i'}$ is related to the original coordinates $x_i$ as follows:

$$x_{i'} = r_i x_i + t_i, \tag{10}$$

where $r_i$ is the rotation matrix. $x_i$ and $x_{i'}$ are measured in pixels in the local image coordinate system, with the top right corner of the image as origin.

In certain embodiments, each transformation is dominated by a global transform introduced during the placement of the TMA at each staining/bleaching round. This implies that there is a global rotation angle Θ and a global translation $T = [T_x, T_y]^T$ that is common to all the spots on the TMA. A point in an image in the TMA coordinate system may be $X_i = [X_i, Y_i]^T$ and the same point after registration may be $X_{i'} = [X_{i'}, Y_{i'}]^T$. $X_i$ and $X_{i'}$ are measured in μm in the TMA coordinate system, with the origin at the top right corner of the first image. If $D_i$ is the TMA coordinates of the top left corner of the image of tissue sample i on the TMA slide as recorded by the microscope, and p is the pixel size in μm, then the TMA coordinates are related to the local image coordinates by the relations $$X_i = p x_i + D_i \text{ and } X_{i'} = p x_{i'} + D_i. \tag{11}$$

In one embodiment, the coordinates of the first TMA spot may be used as the origin of the coordinate system. The slide may be moved such that image of the first TMA spot is comparable to the image of the first TMA spot on the reference image. The relationship between the original and transformed TMA coordinates is expressed as $$X_{i'} = R X_i + T + \xi_i, \tag{12}$$

where R is the global rotation matrix and $\xi_i$ is the residual error associated with local transformations not accounted for by the global transform (e.g., due to the microscope stage). It follows that $$\xi_i = X_{i'} - R X_i - T. \tag{13}$$

For all the N images on the TMA, it may be advantageous to estimate R and T such that $\xi_i$ is minimized, i.e., find R and T such that $$\operatorname{argmin}_{(R,T)} f(R, T) = \sum_{i=1}^{N} \|\xi_i\|^2 \text{ subject to } R^T R = I. \tag{14}$$

The mean may be computed for X and X' and denoted by $\overline{X}$ and $\overline{X}'$ respectively and the correlation matrix may be expressed as:

$$K = \sum_{i=1}^{N} (X_{i'} - \overline{X}')(X_i - \overline{X})^T. \qquad (15)$$

A singular value decomposition (SVD) of the correlation matrix gives a diagonal matrix D and two unitary matrices V and U such that $K=VDU^T$. The rotation matrix R is estimated from the SVD as:

$$\hat{R} = V \begin{pmatrix} 1 & 0 \\ 0 & \det(VU^T) \end{pmatrix} U^T \qquad (16)$$

and the translation estimated as $$\hat{T} = \frac{1}{N} \sum_{i=1}^{N} N(X_{i'} - RX_i) \qquad (17)$$

The robustness of the algorithm was further improved by using the Least Median of Squares estimation method to randomly select a subset of the data to be used for the estimation of the global parameters. In certain embodiments, the algorithm may be used even with (theoretically) up to 50% registration failures.

In step 70, the residual error of registration for each image in the TMA is calculated using equation 13 by substituting the estimated values of R and T. In certain implementations, rather than using a single point to compute residual error, several points on a grid on the image may be sampled, taking the average residual error to be the residual error of the image. The median of the residuals for all images in the TMA was then computed. Based on the assumption that most of the images are correctly registered, a failed registration may be defined as one where $$\xi_i - \text{median}(\xi) > E; \forall i, \qquad (18)$$

where E is a user-defined threshold value. For validation of the proposed method, the images in the data set were registered using sub-optimal registration parameters that gives about 15% registration failures (Run 5 in Table 1). In one experiment, out of 1,612 images evaluated as described, there was 1 false positive and 3 false negatives. This implies a sensitivity of 96.6% and a specificity of 99.9%.

In certain embodiments, registration success rate may be improved by initializing with transformation values that reflect the actual misalignment between the two images, as in step 72. Since the relative locations of tissue images are fixed on a TMA slide, it is may be assumed that the rotation of each image i is due to the global rotation of the slide, i.e., $$r_i = R. \qquad (19)$$

But the translation of each image depends on its location in the TMA slide. This may be deduced from equation 11 in which the residual error $\xi_i$ may be very close to zero in cases of correct registration. So, $$t_i \approx \frac{1}{p}(X_{i'} - RX_i). \qquad (20)$$

The values θ from $r_i$ and $t_x$, $t_y$ from $t_i$ are then used for initializing the registration. In one experiment, to validate the above formulation, sub-optimal registration parameters were used to register all the images. The registration failure detection algorithm found 85 images that were mis-registered. The initial values for each image was individually computed as shown above, using their coordinates in the TMA. Out of the 85 images, 73 were correctly registered in this process, thus leaving only 12 images for manual initialization. This implies that 1,600 images in all were automatically registered using sub-optimal registration parameters, an accuracy of 99.56%.

In chemical bleaching multiplexing approaches, tissue cores sometimes degrade after multiple rounds of staining and bleaching. This is partly due to the effect of bleaching on the tissue, but it is more commonly due to stress induced on the TMA slide by the removal of the cover slip for each round of bleaching. The present techniques include automated tissue quality assessment by registering the tissue core image after a given round of staining or bleaching (say, image B) to the corresponding baseline image before any staining round (say, image A) and then computing image-based metrics to estimate tissue loss or folding. In certain embodiments, the following image-to-image metrics may be appropriate.

In one embodiment, the Mean Squares (MS) Image-to-Image Metric computes the mean squared pixel-wise difference in intensity between the two images as follows:

$$MS(A, B) = \frac{1}{N} \sum_{i=1}^{N} (A_i - B_i)^2, \qquad (21)$$

where $A_i$ and $B_i$ are the ith pixel of images A and B respectively, and N is the number of pixels considered. N is the same in both images and corresponds to the number of pixels in the overlapping region after image registration.

In another embodiment, Normalized Correlation (NC) Image-to-Image Metric computes pixel-wise cross-correlation of the images and normalizes it by the square root of their autocorrelation:

$$NC(A, B) = \frac{\sum_{i=1}^{N}(A_i \cdot B_i)}{\sqrt{\sum_{i=1}^{N} A_i^2 \sum_{i=1}^{N} B_i^2}}. \qquad (22)$$

In additional embodiments, Mean Reciprocal Square Difference (MRS) Image-to-Image Metric computes pixel-wise differences and adds them after passing them through a bell-shaped reciprocal function:

$$MRS(A, B) = \frac{1}{N} \sum_{i=1}^{N} \frac{1}{1 + \frac{(A_i - B_i)^2}{\lambda^2}}, \qquad (23)$$

where λ controls the granularity of tolerable differences. Mutual Information (MI) Image-to-Image Metric measures how much information one image tells about the other. Mutual information is high when both images are very similar, and low otherwise. It is represented as:

$$MI(A,B) = H(A) + H(B) - H(A,B), \qquad (24)$$

where H(A) is the entropy of image A, and H(A,B) is the joint entropy. Normalized Mutual Information (NMI) Image-to-Image Metric normalizes the individual entropies by the joint entropy:

$$NMI(A, B) = \frac{H(A) + H(B)}{H(A, B)}. \quad (25)$$

A Correlation Coefficient (CC) Image-to-Image Metric computes the cross correlation coefficient between intensities in the two images. The optimal value is 1, and images in which the tissue is preserved have values close to 1. The metric is obtained by dividing the covariance with individual standard deviations:

$$CC(A, B) = \frac{Cov(A, B)}{\delta_A \delta_B}. \quad (26)$$

In addition to registration techniques, the tissue quality may be evaluated by counting nuclei in the tissue spots of a TMA image. In the DAPI images used in the experiments described below, the nuclei are clearly visible. The present techniques identify spots with little or no tissue by counting the nuclei in the image. A simple algorithm based on thresholding and morphological operations may be used to count the nuclei. First, the image is converted to binary using a threshold value obtained by the Otsu's method, described in "A threshold selection method from gray level histograms," (IEEE) Trans. Systems, Man and Cybernetics, Vol. 9, pp. 62-66, 1979.

This is followed by morphological binary erosion of the image by 1 pixel to separate the pixels into individual nuclei, which are then counted using a connected component algorithm. In certain embodiments, a nuclei count below 30 is an indication of little or no tissue in the core.

In addition to tissue quality determinations, the present techniques provide an absolute location identifier for tissue spots on a given TMA. To match tissue spots across serial sections of TMAs, the absolute row and column indices based on the arrangement on the TMA recipient block may be used. This is consistent for all TMA serial sections from the same block. A tissue core image identified as, for example, R10C03 (row 10, column 3) in a given TMA corresponds to the same recipient block with the same row column labels on another TMA from the same block. This also implies that TMA spots with the same absolute location identifier have the same clinical information and may be related to one another. The absolute location identifier is computed automatically by registering a TMA-layout image to a similar image of a complete TMA from the same TMA block, and decides the best matches. Each tissue spot is then assigned an absolute location identifier that is consistent across serial sections.

With the forgoing in mind, the following examples illustrate specific embodiments of the present techniques. In one embodiment, a TMA used for validation of the proposed system consisted of 177 tissue locations or spots from 55 randomly selected breast cancer patients and 16 normal breast tissue samples. Each spot had a small sample of breast tissue sectioned at 5 µm. The image acquisition protocol consisted of 13 sequential rounds of staining with different fluorescently-labeled antibodies and bleaching. For this experiment the TMA is labeled with AR, ER, p53, Her2, smooth muscle actin, keratin, pan-cadherin biomarkers. After capturing individual tissue images, the dyes were removed with a bleaching agent, and the tissues were re-stained for another biomarker. The image of nuclear stain 4,6-diamidino-2-phenylindole (DAPI) was also captured for each image in each round of staining/bleaching. This was used as the common image channel, independent of the particular biomarker, to register all the images in each round. Thirteen sets of fluorescent images were acquired, resulting in 2301 images. With each round of staining, a few tissue samples were folded while some others were lost. To be able to calculate the classification rates, each tissue image was also manually examined and classified into 'good tissue', 'partially folded tissue', and 'substantial tissue loss'. Each core with little or no tissue was manually labeled as well. The completely damaged tissue spots were excluded from subsequent analysis. The remaining tissues were classified into Set 1 (good tissues) and Set 2 (partially damaged tissues).

The image of each TMA spot was automatically captured with a Zeiss AxioImager microscope at 20× magnification, traversing the TMA in a zig-zag pattern. Before any round of staining, an operator placed the TMA slide on the microscope, rigidly fixed the top left corner, and calibrated the microscope by recording the relative coordinates of each TMA spot on the microscope. After each round of staining, the operator positioned the TMA rigidly as before and made manual adjustments to obtain a view of the first spot that corresponded to the view obtained in the first imaging round. The microscope then automatically computed the new coordinates of the other spots relative to the first spot using the coordinates saved in the first round. The resulting gray scale images were 12-bit TIFF format with a size of 1344×1024 pixels.

Figure 7B:
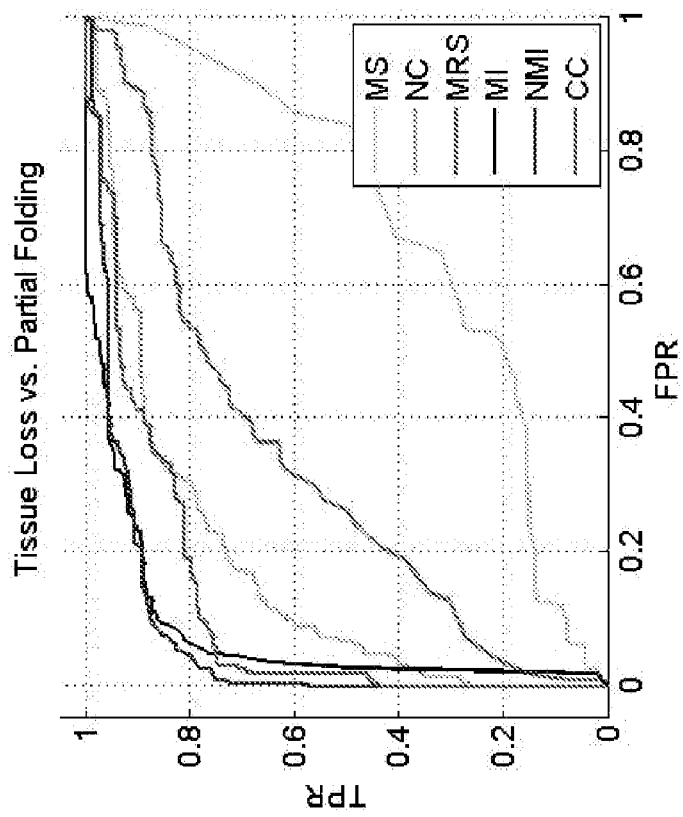
FIG. 7B is a graph of the ROC curves for detecting tissue loss or folded tissue in accordance with aspects of the present technique.
Figure 7A:
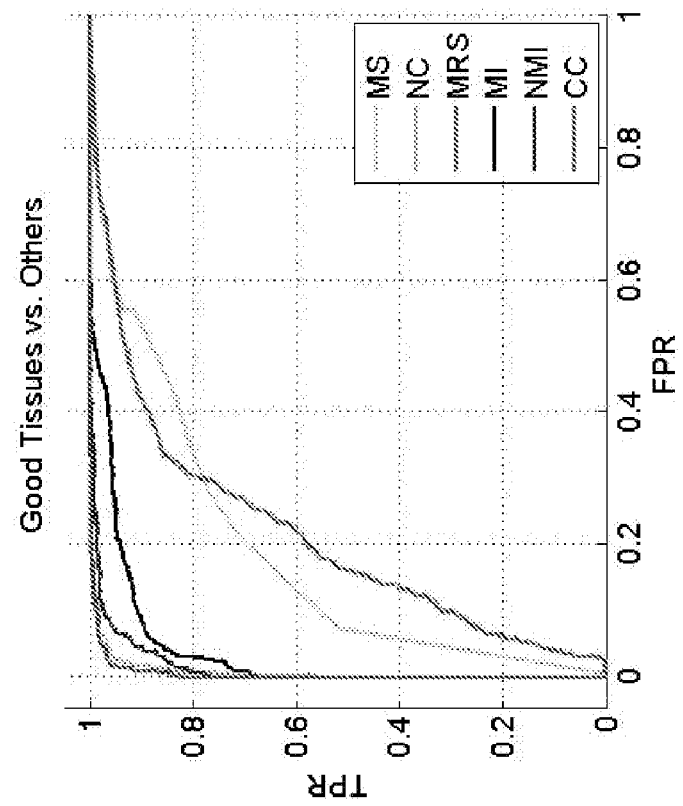
FIG. 7A is a graph of the Receiver Operating Characteristic (ROC) curves for detecting good tissue in accordance with aspects of the present technique.

The 2301 (13 sequential steps on a TMA with 177 tissue spots) images of the experimental data set were evaluated by registering each image to the corresponding baseline image, and computing the image-to-image metric values. The ability of each metric to separate the tissues based on quality was assessed using Receiver-Operating Characteristic (ROC) plots, shown in FIG. 7A and FIG. 7B. Selecting different threshold values for each metric, and comparing the resulting classification with manually labeled images, the True Positive Rates (TPR) and False Positive Rates (FPR) for identifying good tissue (compared to folded or lost tissue) at each threshold point was computed. A similar evaluation was done to distinguish lost tissue from partially folded ones. As depicted in FIG. 7A, correlation coefficient (CC) and normalized correlation (NC) metrics were able to identify good tissues. Mutual information (MI) and normalized mutual information (NMI) metrics performed well in separating partially folded and lost tissue samples in FIG. 7B. CC gave 98.0% true positive rate at 4.9% false positive rate. In separating tissues with partial folding from those with substantial folding, CC gave about 76.1% true positive rate at a similar false positive rate (4.9%). MI and NMI gave better higher true positive rates than CC, but only at higher rates of false positive detection. Using the CC metric, Table 3 summarizes the performance in the automatic assessment of tissue quality. The automatic classification of tissues was compared to the manual labeling of a single individual. About 94.4% of the images fall on the diagonal of the matrix, indicating correct classification.

TABLE 3

Automatic Classification of Tissue Images.

|  |  | Manual Classification | | |
|---|---|---|---|---|
|  |  | Good Tissue | Partial Fold | Tissue Loss |
| TMA-Q | Good Tissue | 1793 | 23 | 0 |
| Classification | Partial Fold | 36 | 191 | 59 |
|  | Tissue Loss | 0 | 11 | 188 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for analyzing a tissue microarray, comprising the steps of:
   using a processor-based computer:
      accessing two or more images of a tissue microarray using the computer, the two or more images comprising a plurality of tissue spots;
      registering corresponding tissue spots on the two or more images using default registration parameters stored on the computer;
      determining the quality of each of the plurality of tissue spots using the computer;
      generating an output on the computer indicating the registration quality of the plurality of spots between the two or more images and the quality of the plurality of tissue spots in at least one of the two or more images, wherein generating the output comprises generating a tissue quality indicator and a registration indicator for each of the plurality of tissue spots in at least one of the two or more images;
      determining if the registration is successful based on the output; and
      changing the default registration parameters in response to an unsuccessful registration.

2. The method of claim 1, wherein at least one of the images is simulated based on the coordinates of the plurality of tissue spots or wherein at least one of the images comprises a whole slide image.

3. The method of claim 1, wherein the two or more images comprises sequentially stained images of the tissue microarray.

4. The method of claim 1, wherein determining the quality of each of the plurality of tissue spots comprises detecting if there is tissue folding or tissue loss in each of the plurality of tissue spots.

5. The method of claim 1, wherein determining the quality of each of the plurality of tissue spots comprises counting cell nuclei in each of the plurality of tissue spots in the two or more images.

6. The method of claim 1, wherein generating the output comprises generating a spreadsheet in which the plurality of spots is assigned a row and column number.

7. The method of claim 1, wherein generating the output comprises generating an overview image in which image data representing each of the plurality of spots are shown within the overview image.

8. The method of claim 1, wherein generating the output comprises generating a chart or graph of each tissue quality indicator or registration indicator for each of the plurality of tissue spots in at least one of the two or more images.

9. A non-transitory computer-readable medium comprising instructions for:
   accessing two or more images of a tissue microarray comprising a plurality of tissue spots;
   registering corresponding tissue spots on the two or more images using default registration parameters;
   determining the quality of each of the plurality of tissue spots;
   generating an output indicating the registration quality of the plurality of spots between the two or more images and the quality of the plurality of tissue spots in at least one of the two or more images, wherein generating the output comprises generating a tissue quality indicator and a registration indicator for each of the plurality of tissue spots in at least one of the two or more images;
   determining if the registration is successful based on the output; and
   changing the default registration parameters in response to an unsuccessful registration.

10. The non-transitory computer-readable medium of claim 9, wherein at least one of the images is simulated based on the coordinates of the plurality of tissue spots or wherein at least one of the images comprises a whole slide image.

11. The non-transitory computer-readable medium of claim 9, wherein the two or more images comprises sequentially stained images of the tissue microarray.

12. The non-transitory computer-readable medium of claim 9, wherein determining the quality of each of the plurality of tissue spots comprises detecting if there is tissue folding or tissue loss in each of the plurality of tissue spots.

13. The non-transitory computer-readable medium of claim 9, wherein determining the quality of each of the plurality of tissue spots comprises counting cell nuclei in each of the plurality of tissue spots in the two or more images.

14. The non-transitory computer-readable medium of claim 9, wherein generating the output comprises generating a spreadsheet in which the plurality of spots is assigned a row and column number.

15. The non-transitory computer-readable medium of claim 9, wherein generating the output comprises generating an overview image in which image data representing each of the plurality of spots are shown within the overview image.

16. The non-transitory computer-readable medium of claim 9, wherein generating the output comprises generating a chart or graph of each tissue quality indicator or registration indicator for each of the plurality of tissue spots in at least one of the two or more images.

17. An image analysis system comprising:
    a processor adapted to access two or more images of a tissue microarray comprising a plurality of tissue spots, the processor adapted to run instructions for:
    registering corresponding tissue spots on the two or more images using default registration parameters;
    determining the quality of each of the plurality of tissue spots;
    generating an output indicating the registration quality of the plurality of spots between the two or more images and the quality of the plurality of tissue spots in at least one of the two or more images, wherein generating the output comprises generating an overview image in which image data representing each of the plurality of spots are shown within the overview image;
    determining if the registration is successful based on the output; and
    changing the default registration parameters in response to an unsuccessful registration.

18. The image analysis system of claim 17, wherein generating the output comprises generating a spreadsheet in which the plurality of spots is assigned a row and column number based on a master map.

19. The image analysis system of claim 17 wherein generating the output comprises generating a tissue quality indicator and a registration indicator for each of the plurality of tissue spots in at least one of the two or more images.

20. The image analysis system of claim 19, wherein generating the output comprises generating a chart or graph of each tissue quality indicator or registration indicator for each of the plurality of tissue spots in at least one of the two or more images.

21. A method for analyzing a tissue microarray, comprising the steps of:

using a processor-based computer:
accessing two or more images of a tissue microarray using the computer, the two or more images comprising a plurality of tissue spots;
registering corresponding tissue spots on the two or more images using default registration parameters stored on the computer;
determining the quality of each of the plurality of tissue spots using the computer;
generating an output on the computer indicating the registration quality of the plurality of spots between the two or more images and the quality of the plurality of tissue spots in at least one of the two or more images, wherein generating the output comprises generating an overview image in which image data representing each of the plurality of spots are shown within the overview image;
determining if the registration is successful based on the output; and
changing the default registration parameters in response to an unsuccessful registration.

22. The method of claim 21, wherein at least one of the images is simulated based on the coordinates of the plurality of tissue spots or wherein at least one of the images comprises a whole slide image.

23. The method of claim 21, wherein the two or more images comprises sequentially stained images of the tissue microarray.

24. The method of claim 21, wherein determining the quality of each of the plurality of tissue spots comprises detecting if there is tissue folding or tissue loss in each of the plurality of tissue spots.

25. The method of claim 21, wherein determining the quality of each of the plurality of tissue spots comprises counting cell nuclei in each of the plurality of tissue spots in the two or more images.

26. The method of claim 21, wherein generating the output comprises generating a spreadsheet in which the plurality of spots is assigned a row and column number.

\* \* \* \* \*